United States Patent
Ohno et al.

(10) Patent No.: US 12,220,426 B2
(45) Date of Patent: Feb. 11, 2025

(54) TYPE 1 HELPER T CELL-INCREASING AGENT, FOOD AND PHARMACEUTICAL

(71) Applicant: DAICEL CORPORATION, Osaka (JP)

(72) Inventors: Hiroshi Ohno, Wako (JP); Tadashi Takeuchi, Wako (JP); Shu Shimamoto, Tokyo (JP); Shuuji Yoshioka, Tokyo (JP); Eiji Miyauchi, Wako (JP); Hiroki Negishi, Wako (JP)

(73) Assignee: DAICEL CORPORATION, Osaka (JP)

( * ) Notice: Subject to any disclaimer, the term of this patent is extended or adjusted under 35 U.S.C. 154(b) by 875 days.

(21) Appl. No.: 17/284,927

(22) PCT Filed: Oct. 24, 2019

(86) PCT No.: PCT/JP2019/041599
§ 371 (c)(1),
(2) Date: Apr. 13, 2021

(87) PCT Pub. No.: WO2020/085407
PCT Pub. Date: Apr. 30, 2020

(65) Prior Publication Data
US 2021/0379097 A1    Dec. 9, 2021

(30) Foreign Application Priority Data

Oct. 25, 2018  (JP) ................................ 2018-201181

(51) Int. Cl.
*A61K 31/717* (2006.01)
*A23L 33/10* (2016.01)
*A61P 35/00* (2006.01)

(52) U.S. Cl.
CPC ............ *A61K 31/717* (2013.01); *A23L 33/10* (2016.08); *A61P 35/00* (2018.01)

(58) Field of Classification Search
None
See application file for complete search history.

(56) References Cited

U.S. PATENT DOCUMENTS

| | | | |
|---|---|---|---|
| 5,366,738 | A | 11/1994 | Rork et al. |
| 5,840,860 | A | 11/1998 | Annison et al. |
| 2010/0233207 | A1 | 9/2010 | Tsuji et al. |
| 2011/0014345 | A1 | 1/2011 | Pilling |

FOREIGN PATENT DOCUMENTS

| | | | | | |
|---|---|---|---|---|---|
| EP | 1127608 | A1 * | 8/2001 | ......... | B01D 67/0011 |
| JP | 5-255071 | A | 10/1993 | | |
| JP | 9-505060 | A | 5/1997 | | |
| JP | 2003-63991 | A | 3/2003 | | |
| JP | 2009-538337 | A | 11/2009 | | |
| JP | 4621218 | B2 | 1/2011 | | |
| JP | 2011-512827 | A | 4/2011 | | |
| WO | WO-2018174141 | A1 * | 9/2018 | ............. | A23L 33/10 |

OTHER PUBLICATIONS

International Preliminary Report on Patentability for International Application No. PCT/JP2019/041599, dated Mar. 3, 2021.
International Search Report for International Application No. PCT/JP2019/041599, dated Dec. 24, 2019.
Park et al., "Short-chain fatty acids induce both effector and regulatory T cells by suppression of histone deacetylases and regulation of the mTOR-S6K pathway," Immunology, vol. 8, No. 1, Jan. 2015, pp. 80-93.
Tayama et al., "Viable count and viability of Bifidobacterium bacteria in fermented milk products on the market," Journal of the Integrated Study Dietary Habits, vol. 24, No. 2, 2013, pp. 118-123, with English abstract.
Extended European Search Report for European Application No. 19874825.3, dated Jul. 14, 2022.
Tasaki et al., "Protective immunity is induced in murine colon carcinoma cells by the expression of interleukin-12 or interleukin-18, which activate type 1 helper T cells", Cancer Gene Therapy, Nature Publishing Groups US, New York, vol. 7, No. 2, Feb. 1, 2000, pp. 247-254.

* cited by examiner

*Primary Examiner* — Traviss C McIntosh, III
(74) *Attorney, Agent, or Firm* — Birch, Stewart, Kolasch & Birch, LLP

(57) ABSTRACT

An object is to provide a Th1-increasing agent that can reduce constraints on storage conditions and feeding form and sufficiently increase Th1 at lower doses. A Th1-increasing agent containing a cellulose derivative as an active ingredient, the cellulose derivative having a degree of butyryl substitution of 0.3 or greater and 2.6 or less, and a total degree of substitution of 0.5 or greater and 2.8 or less.

11 Claims, 4 Drawing Sheets

TYPE 1 HELPER T CELL-INCREASING AGENT, FOOD AND PHARMACEUTICAL

TECHNICAL FIELD

The present invention relates to a type 1 helper T cell-increasing agent, a food, and a pharmaceutical.

BACKGROUND ART

The immune system is a defense mechanism that protects organisms from foreign substances such as pathogens, virally infected cells, and cancer cells, and in this mechanism, leukocytes such as lymphocytes and neutrophils are involved. Lymphocytes include B cells involved in humoral immunity and T cells involved in cell-mediated immunity, and in T cells, CD4-positive T cells and CD8-positive T cells are included.

The majority of the CD4-positive T cells are referred to as helper T cells. Helper T cells are produced in the thymus and are released out of the thymus as naive T cells (immature T cells), and naive T cells activated by antigen stimulation can differentiate into type 1 helper T cells (which may be hereinafter referred to as Th1), type 2 helper T cells (Th2), or type 17 helper T cells (Th17), each having a specific function depending on the extracellular environment such as cytokines present when the native T cells are activated, inducing an optimal immune response for elimination of the antigen. In addition, the majority of CD8-positive T cells can differentiate into cytotoxic T cells (CTL) by antigen stimulation.

Promoting the differentiation into Th1 involves interleukin (IL)-12 and interferon-γ (IFN-γ). IL-12 is produced from dendritic cells and macrophages, and IFN-γ mainly from Th1, natural killer (NK) cells, and the like.

Th1 then produces cytokines, such as interferon-γ (IFN-γ) and interleukin (IL)-2, and these cytokines activate cytotoxic T cells. The cytotoxic T cells then destroy target cells.

Treatments for cancer and the like utilizing an immune system include, in addition to immunotherapy utilizing cytotoxic T cells, immunotherapy utilizing Th1 that assists the activity of cytotoxic T cells, which has been drawing attention.

Patent Document 1 describes a Th1 inducer containing a bacterial cell of a lactic acid bacterium having IL-12-producing and inducing abilities as an active ingredient, the bacterial cell micronized to a particle size of less than 1 micron and prevented from reaggregating by a dispersant or a filler. In addition, "Th1 induction" is described as promoting the differentiation of Th0 cells (naive Th cells) into Th1 by efficiently producing IL-12 from antigen-presenting cells and creating a Th1-dominant state in vivo.

Patent Document 2 describes an oral cytokine inducer containing a microbial bacterial cell carrying a cytokine-inducing substance on the surface. Patent Document 2 also describes the following: "the present invention enables promoting the in vivo production of cytokines, such as IFN-γ and IL-8, which play important roles in immune response, by oral administration and can facilitate the treatment and prevention of many diseases, including infectious diseases, autoimmune diseases, inflammations, and tumors".

Non-Patent Literature 1 describes, as a result of investigating fermented milk and lactic acid bacteria beverage products, when they contain *Bifidobacterium* bacteria, the viable bacteria count was $2 \times 10^6$ to $3 \times 10^8$ cfu/g, and for lactic acid bacteria, the viable bacteria count was $2 \times 10^7$ to $1 \times 10^9$ cfu/g.

CITATION LIST

Patent Document

Patent Document 1: JP 4621218 B
Patent Document 2: JP 2003-063991 A

Non-Patent Literature

Non-Patent Literature 1: Kenji Tayama, et al., "Viable count and viability of *Bifidobacterium* bacteria in fermented milk products on the market", Journal of the Integrated Study of Dietary Habits, Vol. 24, No. 2, p. 118-123, 2013

SUMMARY OF INVENTION

Technical Problem

In Patent Document 1, using a bacterial cell of a lactic acid bacterium to allow murine macrophages to produce IL-12 is described, while the effect of oral administration is not demonstrated.

In addition, Patent Document 2 describes that a transformed lactic acid bacterium administered intragastrically to mice at $5 \times 10^8$ CFU/mouse three times each week significantly induced blood IFN-γ. As shown in Non-Patent Literature 1, since the viable count of *Bifidobacterium* bacteria or lactic acid bacteria is at most approximately $5 \times 10^8$ cfu per gram of fermented milk and lactic acid bacteria beverage, in terms of the amount of the fermented milk or lactic acid bacteria beverage, administration of approximately 3 g per week is required.

Given that an amount of the daily consumption of food for a mouse is approximately 3 g depending on the type and age, 14 wt. % or greater of fermented milk and lactic acid bacteria beverage needs to be administered as a mixed diet. This is an unrealistically large amount when taken by humans, which is an amount painful to take orally as a medication, and an amount impairing enjoyment of a normal diet when taken as a food.

In addition, such a known method of using specific bacteria imposes many constraints on storage conditions or feeding form. For example, as in storage and transportation of fermented milk such as yogurt and a lactic acid bacteria beverage, in order for the intended bacterial to survive and to prevent propagation of other bacteria than the intended bacteria, the intended bacteria needs to be hermetically sealed, refrigerated, and set a relatively short storage period of approximately several weeks.

An object of the present invention is to provide a Th1-increasing agent that can reduce constraints on storage conditions and feeding form and sufficiently increase Th1 at lower doses.

Solution to Problem

A first aspect of the present invention relates to a type 1 helper T cell (Th1)-increasing agent including a cellulose derivative as an active ingredient, the cellulose derivative having a degree of butyryl substitution of 0.3 or greater and 2.6 or less, and a total degree of substitution of 0.5 or greater and 2.8 or less.

In the type 1 helper T cell (Th1)-increasing agent, the cellulose derivative may have a degree of butyryl substitution of 0.3 or greater and 1.5 or less, and a total degree of substitution of 0.5 or greater and 1.5 or less.

The type 1 helper T cell (Th1)-increasing agent may have a degree of acetyl substitution of the cellulose derivative of greater than 0 and 2.5 or less.

The type 1 helper T cell (Th1)-increasing agent may have a degree of acetyl substitution of the cellulose derivative of 0.

In the type 1 helper T cell (Th1)-increasing agent, the cellulose derivative may be a cellulose butyrate or a cellulose acetate butyrate.

A second aspect of the present invention relates to a food containing the type 1 helper T cell (Th1)-increasing agent.

A third aspect of the present invention relates to a food containing the type 1 helper T cell (Th1)-increasing agent, which includes 1 wt. % or greater and 5 wt. % or less of the cellulose derivative.

A fourth aspect of the present invention relates to a pharmaceutical containing the type 1 helper T cell (Th1)-increasing agent.

A fifth aspect of the present invention relates to a pharmaceutical for prevention and/or treatment of a tumor, the pharmaceutical containing the type 1 helper T cell (Th1)-increasing agent.

Advantageous Effects of Invention

The present invention can provide the Th1-increasing agent that can reduce constraints on storage conditions and feeding form and sufficiently increase Th1 at lower doses.

DESCRIPTION OF EMBODIMENTS

Figure 1:
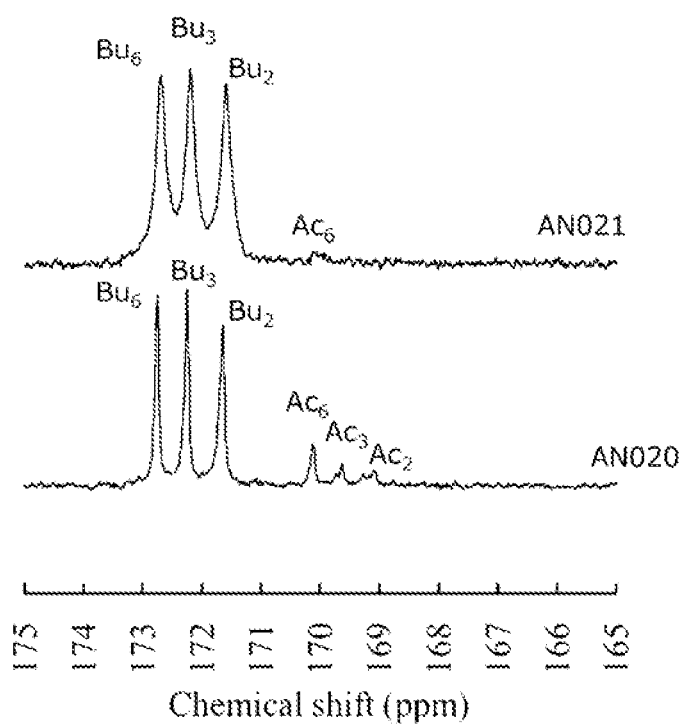
FIG. 1 is a diagram showing a $^{13}$C-NMR spectrum of an acetylated or butyrylated cellulose acetate butyrate.

Hereinafter, an example of a preferred embodiment will be specifically described.

A Th1-increasing agent according to the present disclosure includes a cellulose derivative as an active ingredient, the cellulose derivative having a degree of butyryl substitution of 0.3 or greater and 2.6 or less, and a total degree of substitution of 0.5 or greater and 2.8 or less.

Cellulose Derivative

The cellulose derivative of the present disclosure has a degree of butyryl substitution of 0.3 or greater and 2.6 or less, preferably 0.3 or greater and 1.5 or less, more preferably 0.5 or greater and 1.5 or less, even more preferably 0.7 or greater and 1.4 or less, and most preferably 0.8 or greater and 1.3 or less. With a degree of butyryl substitution of less than 0.3, the amount of butyric acid released in the digestive tract would typically decrease although this would depend on the dose, being less likely to achieve the desired Th1-increasing effect. In addition, with a degree of butyryl substitution of greater than 2.6, the degradation by bacteria such as enterobacteria in the digestive tract would be prevented probably due to the excessively high hydrophobicity, tending to reduce the amount of butyric acid released.

The cellulose derivative according to the present disclosure has a total degree of substitution of 0.5 or greater and 2.8 or less, preferably 0.5 or greater and 2.0 or less, more preferably 0.5 or greater and 1.5 or less, and even more preferably 1.0 or greater and 1.5 or less. With a total degree of substitution of less than 0.5, the amount of butyric acid released in the digestive tract would typically decrease although this would depend on the dose, being less likely to achieve the desired Th1-increasing effect. In addition, with a total degree of substitution of greater than 2.8, the degradation by bacteria such as enterobacteria in the digestive tract would be prevented probably due to the excessively high hydrophobicity, tending to reduce the amount of butyric acid released.

Here, the "degree of butyryl substitution" refers to the sum of the number of butyryl groups replacing the hydrogen atoms of the hydroxyl groups at the positions 2, 3, and 6 per repeating unit of cellulose (glucopyranose unit). The same applies to the degree of substitution with another or other substituent(s), such as the degree of acetyl substitution. In addition, the total degree of substitution refers to the sum of the degree of butyryl substitution and the degree of substitution with another or other substituent(s).

The cellulose derivative of the present disclosure is preferably substituted with only a butyryl group, in other words, values of the degree of butyryl substitution and the total degree of substitution are preferably equal in the cellulose derivative of the present disclosure, from the perspective of delivery of butyric acid to the digestive tract such as the large intestine; however, the cellulose derivative may be substituted with a substituent other than a butyryl group. Examples of the substituent other than a butyryl group include an acetyl group, a carboxyl group, a carboxymethyl group, a 2-hydroxyethyl group, a 2-hydroxypropyl group, and a methyl group. One or some of the 6-positions (hydroxymethyl groups) of the cellulose may be oxidized to a carboxyl group(s). From the perspective of promoting degradation by bacteria, such as enterobacteria, in the digestive tract and increasing the amount of butyric acid to be released, a hydrophilicity is favorably imparted to the cellulose derivative, and from this perspective, among the substituents above, an acetyl group, a carboxymethyl group, or a carboxyl group, which are less hydrophobic than a butyryl group, is effectively introduced. The cellulose derivative may be substituted with one, or two or more of substituent(s) other than a butyryl group.

In particular, the cellulose derivative substituted with an acetyl group, which is less hydrophobic than a butyryl group, as a substituent other than a butyryl group will be described. In producing the cellulose derivative of the present disclosure using, as a raw material, a cellulose, which is relatively difficult to butyrylate due to the high crystallinity or the like, acetic acid is favorably used as an activation treatment agent of the cellulose for performing a pretreatment, or as a medium for an acylation reaction, thus resulting in introducing an acetyl group(s) to the resulting cellulose derivative.

Alternatively, in using a commercially available cellulose acetate butyrate as a raw material and hydrolyzing one or some of its butyryl groups and acetyl groups to obtain the cellulose derivative of the present disclosure, the resulting cellulose derivative contains an acetyl group(s) remaining or introduced as a result of using acetic acid as a medium or the like for such a hydrolysis reaction.

As described above, values of the degree of butyryl substitution and the total degree of substitution are preferably equal in the cellulose derivative of the present disclosure, and the degree of acetyl substitution is preferably 0; however, the cellulose derivative substituted with an acetyl group has a degree of acetyl substitution of preferably greater than 0 and 2.5 or less, and more preferably 0.1 or greater and 1.0 or less.

Here, the cellulose derivative substituted only with a butyryl group is referred to as cellulose butyrate (or butyrylated cellulose), and the cellulose derivative in which its substituent(s) is/are substituted with an acetyl group(s) in addition to a butyryl group(s) is referred to as cellulose acetate butyrate (or butyrylated cellulose acetate or acetylated-butyrylated cellulose).

The degree of substitution of the cellulose derivative can be measured by the following method. For example, the degree of substitution of the cellulose derivative can be measured according to the method described in Tezuka (Tezuka, Carbonydr. Res. 273, 83 (1995)) using NMR. That is, the free hydroxyl group of the cellulose derivative is acylated with a carboxylic anhydride in pyridine. The type of the carboxylic anhydride used here should be selected according to the purpose of the analysis; for example, for the analysis of the degree of butyryl substitution of a cellulose butyrate, acetic anhydride is favorably used. In addition, for example, for a cellulose acetate butyrate, acetic anhydride is favorably used for the analysis of the degree of butyryl substitution, and butyric anhydride is favorably used for the analysis of the degree of acetyl substitution. The resulting sample is dissolved in deuterated chloroform, and the $^{13}$C-NMR spectrum is measured. For example, when the substituent is an acetyl group or a butyryl group, the carbon signals of the acetyl group appear in the region from 169 ppm to 171 ppm in the order of the 2-, 3-, and 6-positions from the high magnetic field; and the carbon signals of the butyryl group appear likewise in the region from 171 ppm to 173 ppm in the order of the positions 2, 3, and 6 from the high magnetic field side. In another example, when a cellulose derivative having a propionyl group or a cellulose derivative having no propionyl group is treated with propionic anhydride for an analytical purpose, and the degree of propionyl substitution is analyzed, the carbonyl carbon signals of the propionyl group appear in the region from 172 ppm to 174 ppm in the same order. The total degree of substitution of the cellulose derivative treated with a carboxylic anhydride by the method of Tezuka or a similar method is 3.0, and thus, each degree of acetyl substitution, butyryl substitution, or propionyl substitution at the positions 2, 3, and 6 of the glucose ring in the cellulose derivative can be determined by normalizing a total sum of the areas of the carbonyl carbon signal of the acyl group originally contained in the cellulose derivative and the carbonyl signal of the acyl group introduced by the carboxylic anhydride treatment to 3.0 and determining the presence ratio of the acetyl group, the butyryl group, and the propionyl group at each corresponding position (in other words, area ratio of each signal) as each degree of substitution. It goes without saying, a substituent containing an acyl group that can be analyzed by this method is only a substituent group that does not correspond to the carboxylic anhydride used in the treatment for an analytical purpose. In addition, the total degree of substitution can be analyzed by $^1$H-NMR in addition to $^{13}$C-NMR.

However, when the total degree of substitution at the positions 2, 3, and 6 of the glucose ring of the cellulose derivative of a sample is 3.0, and all the substituents are known in advance to be limited to substituents, such as an acetyl group and a butyryl group, propionylation can be eliminated, and the NMR spectrum can be measured by dissolving the sample directly in deuterated chloroform. When all the substituents are an acetyl group(s) and a butyryl group(s), the carbon signals of the acetyl group appear in the region from 169 ppm to 171 ppm in the order of the positions 2, 3, and 6 from the high magnetic field, and the carbon signals of the butyryl group appear in the region from 171 ppm to 173 ppm in the same order, as in the treatment including propionylation, and thus the degree of substitution, such as each degree of acetyl substitution and propionyl substitution at the positions 2, 3, and 6 of the glucose ring in the cellulose derivative, can be determined from the presence ratio of the acetyl group and the butyryl group at each corresponding position (in other words, the area ratio of each signal).

A method for producing the cellulose derivative according to the present disclosure is not particularly limited, but the cellulose derivative can be produced, for example, as follows. First, the cellulose derivative can be produced using a cellulose, a cellulose derivative substituted only with an aliphatic acyl group other than a butyryl group or another or other substituent(s), or another or other cellulose derivative(s) having a butyryl group as a raw material, and reacting the raw material cellulose or cellulose derivative with butyric anhydride or butyryl chloride in an organic solvent and in the presence of a catalyst. Examples of the organic solvent include acetic acid, acetone, pyridine, N,N-dimethylacetamide (DMAc), and a solution of lithium chloride in DMAc, and a mixed solvent of these. Among these, a solvent containing at least acetic acid is preferred. Examples of the catalyst include sulfuric acid, pyridine, and N,N-dimethyl-4-aminopyridine.

Second, the cellulose derivative can be produced using a natural cellulose as a raw material, by activating the cellulose as necessary, then acylating the cellulose with an acylating agent in the presence of a sulfuric acid catalyst, and then partially neutralizing, if necessary, to deacylate (hydrolyze or age). In more detail, the cellulose derivative can be produced by activating the cellulose usually with an organic carboxylic acid corresponding to an acyl group, such as acetic acid, propionic acid, and butyric acid (butyric acid in substitution with a butyryl group), then preparing a triacyl ester with an acylating agent, such as acetic anhydride, propionic anhydride, and butyric anhydride (butyric anhydride in butylation), using a sulfuric acid catalyst, decomposing the acid anhydride, and adjusting the degree of acylation by hydrolysis or aging in a carboxylic acid/water system.

Examples of the natural cellulose as a raw material generally include wood pulp or cotton linter. These natural celluloses each have a weight average degree of polymerization from approximately 1500 to 3000 or from 3000 to 6000. In preparing the cellulose derivative of the present disclosure using a natural cellulose as a raw material as described above, the weight average degree of polymerization decreases in the preparation process and may become approximately from 50 to 1500. The weight average degree of polymerization of the cellulose derivative of the present disclosure is not particularly limited, but, for example, from the perspectives of stirring loads in various reaction operations in preparing the cellulose derivative and an amount of a precipitating agent to be used in a precipitation operation after aging, the weight average degree of polymerization is preferably approximately from 100 to 400.

Th1-Increasing Agent

Th1 in the Th1-increasing agent of the present disclosure refers to a T cell differentiated from a naive T cell and predominantly producing interferon-γ (IFN-γ). Th1 is typically a transcription factor T-bet-positive CD4-positive T cell.

The increase in the Th1-increasing agent of the present disclosure includes both meanings of differentiation of naive T cells into Th1, and the proliferation and/or accumulation of Th1 induced by the differentiation. In addition, the increase also includes an increase in any system of in vivo, in vitro, and ex vivo.

Administration of the Th1-increasing agent increases Th1 in the intestinal tract. In addition, the effect of the Th1-increasing agent can be evaluated as follows. Of lymphocytes isolated from an experimental animal such as a mouse administered orally with the Th1-increasing agent, CD3- and CD4-positive cells expressing T-bet are labeled as Th1 in the present disclosure, and the ratio of Th1 can be measured by flow cytometry, where the total number of the isolated lymphocytes is regarded as 100.

The mechanism by which Th1 in the intestinal tract is increased by the administration of the Th1-increasing agent, especially oral administration, is as follows. The cellulose derivative of the present disclosure, which is the active ingredient of the Th1-increasing agent, is not degraded by mammalian digestive enzymes and partially or totally fermented or degraded by enterobacteria. Expected products resulting from the fermentation or degradation of the cellulose derivative by enterobacteria include butyric acid derived from a butyryl group; and short-chain fatty acids (SCFAs), such as acetic acid, propionic acid, and butyric acid, derived from glucose residues. Of these, butyric acid in particular increases preferentially.

The cellulose derivative of the present disclosure has features, such as releasing butyric acid and increasing butyric acid concentration in the intestine, by mechanisms such as being degraded by enterobacteria.

In contrast to a probiotic approach including the direct administration of a particular bacterium as described in Patent Document 2, the administration of the Th1-increasing agent of the present disclosure is to ingeniously devise cellulose as a dietary fiber to provide butyric acid in the intestine and is in a sense a prebiotic approach addressing the environmental aspect for enterobacteria.

Here, probiotics and prebiotics do not conflict with each other and are expected to exert effects synergistically or exert effects complementarily, for example, when one is not effective, the other can work effectively.

The Th1-increasing agent of the present disclosure can take a prebiotic approach. The Th1-increasing agent of the present disclosure is characterized in that it is easy to store the active ingredient and that it has a wide range of options for the form of feeding. For example, the Th1-increasing agent of the present disclosure can be stored at room temperature for about one year, and can also be used as a component in foods baked at a temperature below 200° C., such as breads, cakes, and biscuits.

The Th1-increasing agent of the present disclosure may be contained in foods or pharmaceuticals, and can be used as a component of various foods or pharmaceuticals as follows. Examples of the method of administration include oral administration in particular. Various forms can be selected. For example, the following forms can be employed: common form for pharmaceuticals including powders, granules, tablets, sugar-coated tablets, capsules, syrups, pills, suspensions, liquids and solutions, and emulsions; and common form for foods including beverages; confection products such as gums, chocolates, candies, sweet bean jellies (yokan), and jellies; noodles; baked foods such as breads, cakes, and biscuits; canned foods; retort foods; meat foods of domestic animals; fish paste foods; edible oil compositions such as margarine, dressings, and mayonnaise; nutritional supplements; and milk products such as butter, ice cream, and yogurt. The Th1-increasing agent is preferably taken at a daily dose from 1 g to 10 g to attain the effect in humans, and since a relatively large amount can be taken, sugar-coated tablets; noodles; and baked foods such as biscuits and the like are preferable among the forms listed above. In addition, the Th1-increasing agent of the present disclosure can also be incorporated as a thickening agent in the form of pharmaceuticals or goods.

For a food containing the Th1-increasing agent of the present disclosure, the content of the cellulose derivative is preferably 0.5 wt. % or greater, more preferably 1 wt. % or greater and 5 wt. % or less, and even more preferably 1.5 wt. % or greater and 3 wt. % or less of the food. The food containing the Th1-increasing agent in an amount of the above range can increase Th1 without compromising the taste and texture of the food.

The Th1-increasing agent of the present disclosure contained in a food or pharmaceutical is useful for the prevention and/or treatment (reduction or prevention of adverse effects) of target diseases such as allergic diseases, infectious diseases, and rejection in organ transplantation. Specific examples of such target diseases include the following: sprue, type 1 diabetes mellitus, graft-versus-host rejection following bone marrow transplantation, osteoarthritis, juvenile chronic arthritis, Lyme arthritis, psoriatic arthritis, reactive arthritis, spondyloarthropathy, systemic lupus erythematosus, insulin-dependent diabetes mellitus, thyroiditis, asthma, psoriasis, dermatitis scleroderma, atopic dermatitis, graft-versus-host rejection, acute or chronic immune diseases associated with organ transplantation, sarcoidosis, atherosclerosis, disseminated intravascular coagulation syndrome, Kawasaki disease, Graves' disease (Pasedow disease), nephrotic syndrome, chronic fatigue syndrome, Wegener's granulomatosis, Henoch-Schönlein purpura, microscopic polyangiitis in the kidney, chronic active hepatitis, uveitis, septic shock, toxic shock syndrome, sepsis syndrome, cachexia, acquired immunodeficiency syndrome, acute transverse myelitis, Huntington's disease, Parkinson's disease, Alzheimer's disease, stroke, primary biliary cirrhosis, hemolytic anemia, polyglandular dysfunction syndrome type 1 and polyglandular dysfunction syndrome type 2, Schmidt's syndrome, adult (acute) respiratory distress syndrome, alopecia, alopecia areata, seronegative arthropathy, arthropathy, Reiter's disease, psoriatic arthropathy, chlamydial infection, *Yersinia/Salmonella* infection-related arthropathies, spondyloarthropathy, atheromatous disease/atherosclerosis, allergic colitis, atopic allergies, food allergies (such as peanut allergies, nut allergies, egg allergies, milk allergies, soy allergies, wheat allergies, seafood allergies, shellfish allergies, or sesame allergies), pemphigus vulgaris, pemphigus foliaceus, pemphigoid, linear IgA disease, Coombs' test-positive hemolytic anemia, acquired pernicious anemia, juvenile pernicious anemia, muscular myelitis/Royal Free disease, chronic mucocutaneous candidiasis, giant cell arteritis, primary sclerotic hepatitis, acquired immunodeficiency syndrome, acquired immunodeficiency-related diseases, hepatitis C, common variable immunodeficiency (unclassifiable hypogammaglobulinemia), dilated cardiomyopathy, fibrotic lung diseases, cryptogenic fibrosing alveolitis, postinflammatory interstitial pneumonia, interstitial pneumonia, connective tissue disease-related interstitial lung diseases, mixed connective tissue-related disease lung diseases, systemic sclerosis-related interstitial lung diseases, rheumatoid arthritis-related interstitial lung diseases, systemic lupus erythematosus-related lung diseases, dermatomyositis/polymyositis-related pulmonary diseases, Sjögren disease-related lung diseases, ankylosing spondylitis-related lung diseases, vasculitic diffuse lung diseases, hemosiderosis-related lung diseases, drug-induced interstitial lung diseases, radiation fibrosis, bronchiolitis obliterans, chronic eosinophilic pneumonia, lymphocytic infiltrative lung diseases, postinfectious interstitial pneumonia, gouty arthritis, type B insulin resistance due to acanthosis nigricans, hypoparathyroidism, acute immune diseases associated with organ transplantation, chronic immune diseases associated with organ transplantation, osteoarthritis, primary sclerosing cholangitis, idiopathic leukopenia, kidney disease NOS, glomerulonephritis, microscopic polyangiitis in the kidney, discoid lupus erythematosus, idiopathic male sterility or NOS, multiple sclerosis (related to all subtypes), insulin-dependent diabetes mellitus, sympathetic ophthalmia, connective tissue diseases due to pulmonary hypertension, Goodpasture syndrome, lung symptoms of polyarteritis nodosa, acute rheumatic fever, rheumatoid spondylitis, Still disease, systemic sclerosis, Takayasu disease/arteritis, idiopathic thrombocytopenia, hyperthyroidism, goitrous hypothyroidism (Hashimoto disease), primary myxedema, lens-induced uveitis, primary vasculitis, leukoderma, allergic rhinitis (pollen allergies), anaphylaxis, pet allergies, latex allergies, drug allergies, allergic rhinitis, conjunctivitis, eosinophilic esophagitis, hypereosinophilic syndrome, eosinophilic gastroenteritis, cutaneous lupus erythematosus, eosinophilic esophagitis, hypereosinophilic syndrome, eosinophilic gastroenteritis, diarrhea, and tumors.

Th1 produces cytokines such as interferon-γ (IFN-γ) and interleukin (IL)-2. The increase in Th1 can be expected to help prevent and treat, for example, infectious diseases, inflammations, tumors, and the like through the in vivo production of cytokines, such as IFN-γ. In addition, the increase in Th1 in the intestinal tract such as the small intestine, large intestine, cecum, colon, and rectum, and particularly in the lamina propria of the large intestine is useful for the prevention and/or treatment of tumors and allergies, such as food allergies.

The dosage of the Th1-increasing agent of the present disclosure is administered to an individual in an amount sufficient to provide the desired Th1 increase. Specifically, the dosage can be determined empirically considering the age, weight, gender, health status of an individual; conditions of an individual to receive the Th1-increasing agent, such as status of the stomach, small intestine, large intestine, or the like; the method of administration and the formulation form; and the like. The dose per administration may be, for example, from 12.5 mg/kg body weight to 125 mg/kg body weight or from 25 mg/kg body weight to 75 mg/kg body weight. In addition, the Th1-increasing agent may be administered to an individual once or more than once. When administered more than once, the Th1-increasing agent may be administered at regular or irregular intervals, or as necessary. The appropriate number of administrations can be empirically determined considering of conditions of an individual, the method of administration, the formulation form, and the like in the same manner as for the dosage.

EXAMPLES

Hereinafter, the present invention will be specifically described with reference to examples, but the technical scope of the present invention is not limited by these examples.

Preparation of Cellulose Derivative
Preparation of Regenerated Cellulose (Base-Catalyzed De-Esterification of Cellulose Acetate Butyrate)

To 29.0 L of deionized water, 1.5 kg of sodium hydroxide was added and dissolved. The gas phase in the container was changed to a nitrogen atmosphere, and 2.0 kg of cellulose acetate butyrate (available from Sigma-Aldrich, product No. 419060; hereinafter referred to as the "raw material cellulose acetate butyrate") was added as a raw material, and then 7.0 L of methanol was slowly added. The mixture was kept at 30° C. for 72 hours with stirring. Then, acetic acid was added to adjust the pH to 6.2 to 7. The resulting solid was filtered off, washed using 75 L of deionized water, then dried under reduced pressure at 80° C., and 880.0 g of a white powder was obtained. This is designated as Cell-WSCB. As shown later in "measurement of degree of substitution", the raw material cellulose acetate butyrate has a degree of acetyl substitution of 0.1, a degree of butyryl substitution of 2.5, and a total degree of substitution of 2.6, and Cell-WSCB is a regenerated cellulose having no acetyl or butyryl group.

Dissolution of Cell-WSCB (Regenerated Cellulose)

After 850.0 g of Cell-WSCB (a regenerated cellulose) was suspended in a deionized water/methanol mixture (3.4 L/1.7 L), the suspension was allowed to stand for 30 minutes, and then the liquid phase was filtered off. The resulting wet regenerated cellulose was suspended in 5.7 L of dimethylacetamide (DMAc), the suspension was allowed to stand for 30 minutes, then the liquid phase was filtered off. A series of these operations was repeated four times, and moisture was removed from the wet product of the regenerated cellulose. To the resulting regenerated cellulose wet product were added 1.2 kg of lithium chloride and 15.0 L of DMAc, and the temperature was raised to 100° C. under a nitrogen atmosphere and kept for 1 hour. This mixture was cooled to near room temperature, further cooled to minus 20° C. using dry ice, kept for 1 hour, and then the temperature was raised to near room temperature. A clear regenerated cellulose solution was obtained.

Preparation of Cellulose Butyrate (WSCB)

Under a nitrogen atmosphere, 1.1 L of pyridine was added to the resulting regenerated cellulose solution, and further 1.221 L of butyric anhydride was slowly added. The temperature was then raised to 90° C. and kept for 5 hours. After that, the temperature was reduced to 50° C. 1.0 L of ethanol was slowly added, and a reaction mixture was obtained. At this time, the temperature of the mixture was raised by rising temperature due to the decomposition of the anhydride, but the rate of addition of ethanol was adjusted to keep the temperature always at 75° C. or less. The resulting reaction mixture was slowly added to 110 L of a mixture of tetrahydrofuran (TFH) and deionized water (a volume ratio of 1/1), and a precipitate was formed. The precipitate was washed sequentially with 30 L of deionized water and 30 L of ethanol and dried under reduced pressure at 80° C., and 925.0 g of product was obtained. This is designated as WSCB. As shown later in "measurement of degree of substitution", WSCB is a cellulose butyrate with a degree of acetyl substitution of 0.0, a degree of butyryl substitution of 1.3, and a total degree of substitution of 1.3.

Measurement of Degree of Substitution

Measurement of Degree of Substitution of Raw Material Cellulose Acetate Butyrate (1) Acetylation of Raw Material Cellulose Acetate Butyrate In 12 mL of DMAc, 1.2 g of raw material cellulose acetate butyrate was dissolved. To this solution were added 12 mL of pyridine, 90 mg of N,N-dimethylaminopyridine, and 12 mL of acetic anhydride, and the temperature was raised to 100° C. with stirring under a nitrogen atmosphere and kept for 1 hour. This reaction mixture was cooled to near room temperature and added to 600 mL of a methanol/deionized water mixed solvent (a volume ratio of 1/1), and a precipitate was formed and deliquored. The precipitate was washed three times with 60 mL of a mixed solvent of the same composition. The precipitate was dissolved in 30 mL of acetone. The acetone solution of the precipitate was added to 600 mL of a methanol/deionized water mixed solvent (a volume ratio of 1/1), and a precipitate was formed and deliquored. The precipitate was washed three times with 60 mL of a mixed solvent of the same composition and then dried under reduced pressure at 80° C., and a powdery sample was obtained. The resulting sample is a product formed by acetylating the raw material cellulose acetate butyrate. This is designated as AN020.

The total degree of substitution of the acetyl group and butyryl group of AN020 is 3.0. When the sample obtained by acylation (acetylation) was subjected to a second acylation (acetylation) in the same conditions, the ratios of the acetyl group and the butyryl group (or each degree of substitution of the acetyl group and the butyryl group calculated on the assumption that the total degree of substitution is 3.0) was not changed before and after the second acylation. This verified that the total degree of substitution of the acetyl group and butyryl group was 3.0, in other words, no unsubstituted hydroxyl group was contained.

The resulting AN020 was dissolved in deuterated chloroform, and the $^{13}$C-NMR spectrum was measured. The results are illustrated in FIG. 1. The acetyl and butyryl group signals at the 2-, 3-, and 6-positions of the glucose residues are referred to as $Ac_2$, $Ac_3$, $Ac_6$, $Bu_2$, $Bu_3$, and $Bu_6$, respectively. The carbon signals of the acetyl group appear in the region from 169 ppm to 171 ppm in the order of the 2-, 3-, and 6-positions from the high magnetic field; and the carbon signals of the butyryl group appear in the region from 171 ppm to 173 ppm in the same order. Thus, $Ac_2$, $Ac_3$, $Ac_6$, $Bu_2$, $Bu_3$, and $Bu_6$ each are signals as illustrated in FIG. 1. The total sum of the areas of these signals was assumed to be 3.0, and the ratio of the sum of the areas of $Ac_2$, $Ac_3$, and $Ac_6$ in this total sum and the ratio of the sum of the areas of $Bu_2$, $Bu_3$, and $Bu_6$ in this total sum were each determined as the degree of acetyl substitution and the degree of butyryl substitution. As a result, the degree of butyryl substitution was 2.5.

(2) Butyrylation of Raw Material Cellulose Acetate Butyrate

A powdery sample was obtained in the same manner as in (1) acetylation of raw material cellulose acetate butyrate above with the exception that 12 mL of acetic anhydride was replaced with 18 mL of butyric anhydride. This is designated as AN021. AN021 is a product formed by butyrylating the raw material cellulose acetate butyrate.

The total degree of substitution of the acetyl group and butyryl group of AN021 is also 3.0. When the sample obtained by acylation (butyrylation) was acylated (butyrylated) again in the same conditions, the ratios of the acetyl group and the butyryl group (or each degree of substitution of the acetyl group and the butyryl group calculated on the assumption that the total degree of substitution is 3.0) was not changed before and after the second acylation. This verified that the total degree of substitution of the acetyl group and butyryl group was 3.0, in other words, no unsubstituted hydroxyl group was contained.

The $^{13}$C-NMR spectrum was also measured for AN021 similarly to AN020. The results are shown in FIG. 1. The total sum of the areas of signals of $Ac_2$, $Ac_3$, $Ac_6$, $Bu_2$, $Bu_3$, and $Bu_6$ was assumed to be 3.0, and the ratio of the sum of the areas of $Ac_2$, $Ac_3$, and $Ac_6$ in this total sum and the ratio of the sum of the areas of $Bu_2$, $Bu_3$, and $Bu_6$ in this total sum were each determined as the degree of acetyl substitution and the degree of butyryl substitution. As a result, the degree of acetyl substitution was 0.1.

(3) Degree of Acetyl Substitution and Degree of Butyryl Substitution

The raw material cellulose acetate butyrate has an acetyl group and a butyryl group and further has an unsubstituted hydroxyl group. Thus, the degree of butyryl substitution determined for AN020 obtained by acetylating the unsubstituted hydroxyl group is equal to the degree of butyryl substitution of the raw material cellulose acetate butyrate. In addition, the degree of acetyl substitution determined for AN021 is also equal to the degree of acetyl substitution of the raw material cellulose acetate butyrate. Thus, the raw material cellulose acetate butyrate has a degree of acetyl substitution of 0.1, a degree of butyryl substitution of 2.5, and a total degree of substitution of 2.6.

Measurement of Degree of Substitution of Cell-WSCB (1) Acetylation of Cell-WSCB

After 1.6 g of Cell-WSCB was suspended in 100 mL of deionized water, the suspension was allowed to stand at room temperature for 30 minutes and deliquored with a glass filter (G3), and a wet Cell-WSCB was obtained. The wet Cell-WSCB was suspended in 60 mL of DMAc, and the suspension was allowed to stand at room temperature for 30 minutes and deliquored with a glass filter (G3). A series of these operations was performed five times, 24 mL of DMAc and 2.4 g of lithium chloride were added to the resulting Cell-WSCB, and the temperature was raised to 100° C. with stirring under a nitrogen atmosphere and kept for 1 hour. This mixture was cooled to near room temperature, further cooled to minus 20° C. using dry ice, kept for 1 hour, and then the temperature was raised to near room temperature, and a transparent solution was obtained. To this solution were added 24 ml of pyridine, 180 mg of N,N-dimethylaminopyridine, and 24 mL of acetic anhydride, and the temperature was raised to 100° C. with stirring under a nitrogen atmosphere and kept for 8 hours, and then the reaction mixture was allowed to stand to cool to near room temperature. This reaction mixture was added to 1200 mL of a methanol/deionized water mixed solvent (a volume ratio of 1/1), and a precipitate was formed and deliquored. The precipitate was washed three times with 120 mL of a mixed solvent of the same composition. The resulting precipitate was dissolved in 60 mL of acetone. In this dissolution treatment, the mixture was cooled to minus 20° C., and the temperature of the mixture was raised to near room temperature. The acetone solution of the precipitate was added to 1200 mL of a methanol/deionized water mixed solvent (a volume ratio of 1/1), and a precipitate was formed and deliquored. The precipitate was washed three times with 120 mL of a mixed solvent of the same composition and then dried under reduced pressure at 80° C., and a powdery sample was obtained. This is designated as AN009.

Figure 2:
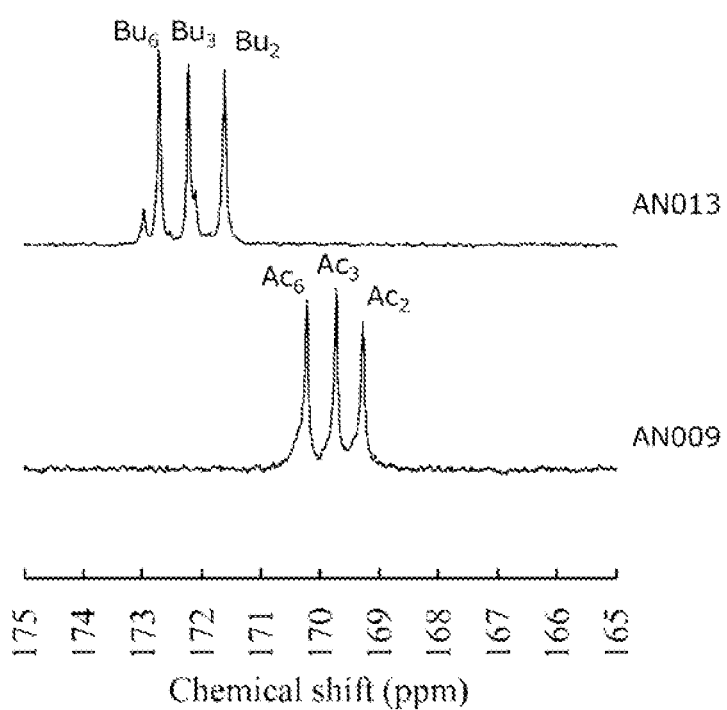
FIG. 2 is a diagram showing a $^{13}$C-NMR spectrum of an acetylated or butyrylated regenerated cellulose.

The resulting AN009 was dissolved in deuterated chloroform, and the $^{13}$C-NMR spectrum was measured similarly to AN020. The results are shown in FIG. 2. In the spectrum of AN009, no signal corresponding to the butyryl group was observed.

(2) Butyrylation of Cell-WSCB

A powdery sample was obtained in the same manner as in (1) acetylation of Cell-WSCB above with the exception that 24 mL of acetic anhydride was replaced with 38 mL of butyric anhydride. This is designated as AN013. AN013 is a product formed by butyrylating Cell-WSCB (a regenerated cellulose).

The resulting AN013 was dissolved in deuterated chloroform, and the $^{13}$C-NMR spectrum was measured similarly to AN020. The results are shown in FIG. 2. In the spectrum of AN013, no signal corresponding to the acetyl group was observed.

(3) Degree of Acetyl Substitution and Degree of Butyryl Substitution

The degree of butyryl substitution determined for the resulting AN009 was 0. A series of treatments to obtain AN009 from CELL-WSCB includes no treatment of adding or eliminating a butyryl group, and thus the degree of butyryl substitution determined for the resulting AN009 is equal to the degree of butyryl substitution of Cell-WSCB (a regenerated cellulose). That is, the degree of butyryl substitution of Cell-WSCB (a regenerated cellulose) is 0.

In addition, the degree of acetyl substitution determined for the resulting AN013 is 0. The degree of acetyl substitution determined for AN013 is also equal to the degree of acetyl substitution of Cell-WSCB. Thus, the degree of acetyl substitution of Cell-WSCB is 0. Thus, Cell-WSCB obtained by base-catalyzed deesterification of the raw material cellulose acetate butyrate has a degree of acetyl substitution of 0 and a degree of butyryl substitution of 0. That is, this confirmed that Cell-WSCB was a regenerated cellulose.

Measurement of Degree of Substitution of Cellulose Butyrate (WSCB)

A powdery sample was obtained by acetylating the cellulose butyrate (WSCB) in the same manner as in (1) acetylation of raw material cellulose acetate butyrate above with the exception that the raw material cellulose acetate butyrate was replaced with the cellulose butyrate (WSCB). This is designated as AN004.

Figure 3:
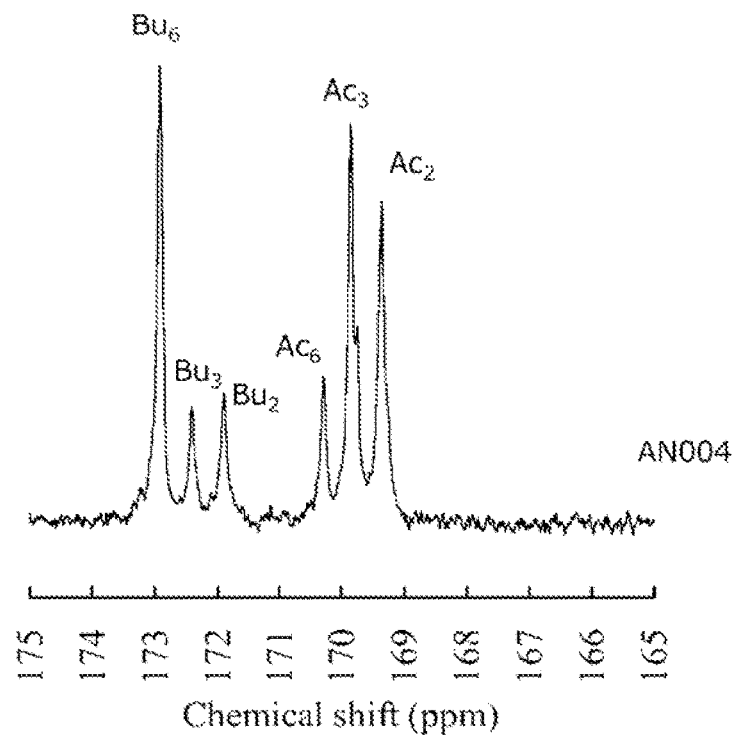
FIG. 3 is a diagram showing a $^{13}$C-NMR spectrum of an acetylated cellulose butyrate.

The resulting AN004 was dissolved in deuterated chloroform, and the $^{13}$C-NMR spectrum was measured similarly to AN020. The results are shown in FIG. 3.

Cell-WSCB has no acetyl group, and thus the acetyl groups shown in the spectrum of AN004 are all thought to have been introduced in the subsequent acetylation. On the other hand, the butyryl groups shown in the spectrum of AN004 are all thought to be derived from WSCB. The total degree of substitution of the acetyl group and butyryl group of AN004 is also 3.0. The total sum of the areas of signals of $Ac_2$, $Ac_3$, $Ac_6$, $Bu_2$, $Bu_3$, and $Bu_6$ was assumed to be 3.0, and the ratio of the sum of the areas of $Ac_2$, $Ac_3$, and $Ac_6$ in this total sum and the ratio of the sum of the areas of $Bu_2$, $Bu_3$, and $Bu_6$ in this total sum were each determined as the degree of acetyl substitution and the degree of butyryl substitution. The butyryl substitution was 1.3.

A series of treatments to obtain AN004 from WSCB includes no treatment of adding or eliminating a butyryl group, and thus the degree of butyryl substitution determined for the resulting AN004 is equal to the degree of butyryl substitution of the cellulose butyrate (WSCB). Thus, the degree of butyryl substitution of the cellulose butyrate (WSCB) is 1.3.

Measurement of Degree of Polymerization of Cellulose Butyrate (WSCB)

The molecular weights in terms of polystyrene (weight average molecular weight and number average molecular weight) of AN004 obtained by acetylating WSCB in the method described above were measured by GPC (SEC), and further the degrees of polymerization (weight average degree of polymerization and number average degree of polymerization) were determined as the degree of polymerization of WSCB according to the following formula.

$$\text{Degree of polymerization} = \text{molecular weight}/(162.14 + \text{degree of butyryl substitution} \times 70.091 + (3 - \text{degree of butyryl substitution}) \times 42.037)$$

Molecular weight: weight average molecular weight or number average molecular weight The GPC measurement was performed under the following conditions.

Solvent: tetrahydrofuran
Sample concentration: 0.2% (wt/vol)
Column: Shodex KF-804 and KF-805
Temperature: 30° C.
Flow rate: 1 mL/min
Sample injection volume: 50 μL
Detection: differential refractive index detector
Polystyrene standards: Shodex SM-105 (molecular weights of 2700000, 1390000, 661000, 323000, 124000, 47200, 18300, 6940, 2980, and 1220)

The weight average degree of polymerization of WSCB thus determined was 254 and the number average degree of polymerization was 128.

Evaluation of Th1 Increase

Preparation of Feed

Purified feed AIN-93G (REEVE et al., Journal of Nutrition, 123, 1939-1951 (1993)) containing 5 wt. % of cellulose was processed to obtain a feed in which all the cellulose was replaced with WSCB (which may be hereinafter referred to as WSCB-AIN-93G), and this was used as a butyric acid diet. In addition, a feed in which all the cellulose was replaced with Cell-WSCB (which may be hereinafter referred to as Cell-WSCB-AIN-93G) was used as a normal diet.

Experimental Animal

C57BL/6J strain male mice aged 3 weeks were used.

Rearing Experiment

Given Cell-WSCB-AIN-93G, 10 individual mice were reared for one week (preliminary rearing). Mice were then grouped into two groups each with five individuals and reared for another four weeks. During this period, one group was given Cell-WSCB-AIN-93G, and this group was designated as the normal diet group. The other group was given WSCB-AIN-93G, and this group was designated as the butyric acid diet group. Each diet was given ad libitum.

Cell Separation and Flow Cytometry

To isolate lymphocytes from the large intestinal lamina propria of the mice reared, the large intestine was collected, longitudinally cleaved, and washed to remove feces and the like in the large intestine. Then, the washed large intestine was shaken in 5 mM EDTA-containing HBSS at 37° C. for 20 minutes. After removing epithelial cells and adipose tissue, intestinal tissue was finely cut into small slices, the RPMI 1640 medium (2% fetal bovine serum (FBS), 400 U/mL collagenase D (Roche Diagnostics K.K.), 0.25 U/mL dispase (CORNING), and 0.1 mg/mL DNase I (WAKO)) was added, and the mixture was shaken in a water bath at 37° C. for 1 hour. The digested tissue was washed with 5 mM EDTA-containing HBSS, resuspended in 5 mL of 35%

Percoll (GE Healthcare), and layered onto 2.5 mL of 70% Percoll in a 15-mL Falcon tube. The cells were then centrifuged at 2000 rpm for 20 minutes under room temperature and separated by Percoll density gradient. The interface cells were collected and used as lamina propria lymphocytes.

Staining of Th1

The collected cells were suspended in a staining buffer (PBS, 2% FBS) and stained using the PerCP/Cy 5.5-labeled anti-CD3e antibody (145-2C11, Biolegend) and the APC-eflour 780-labeled anti-CD4 antibody (RM4-5, eBiosciences). After staining CD3e and CD4, intracellular Foxp3 and T-bet were stained using the Foxp3 Staining Buffer Set (eBioscience), the PE-labeled anti-Foxp3 antibody (FJK-16s, cBioscience), and the PE/cy7-labeled anti-T-bet (4B-10, Biolegend).

INF-γ Production Stimulation and Staining

To examine the ability to produce INF-γ, the major cytokine of Th1, to the collected cells were added the RPMI 1640 medium (10% FBS (Roche), 0.1 mM HEPES, 100 unit/mL penicillin, 100 μg/mL streptomycin, 2 mM L-glutamine, and 0.1 mM 2-mercaptoethanol (all from Thermo Fisher Scientific)) supplemented with 25 ng/mL PMA, 1 μg/mL ionomycin (both from Shigma-Aldrich), and 5 μg/mL Brefeldin A Solution (Biolegend), and the cells were cultured in a $CO_2$ incubator at 37° C. for 4 hours. After washed, the cells were suspended in a staining buffer (PBS, 2% FBS) and stained using the PerCP/Cy 5.5-labeled anti-CD3e antibody (145-2C11, Biolegend) and the APC-eflour 780-labeled anti-CD4 antibody (RM4-5, eBiosciences). After staining CD3e and CD4, intracellular INF-γ was stained using the Foxp3 Staining Buffer Set (eBioscience) and the FITC-labeled anti-INF-γ antibody (XMG 1.2, Biolegend).

Flow cytometry was then performed using FACScant II, and data were analyzed with FlowJo software (TreeStar Inc.).

Flow Cytometry Results of Th1

Figure 4:
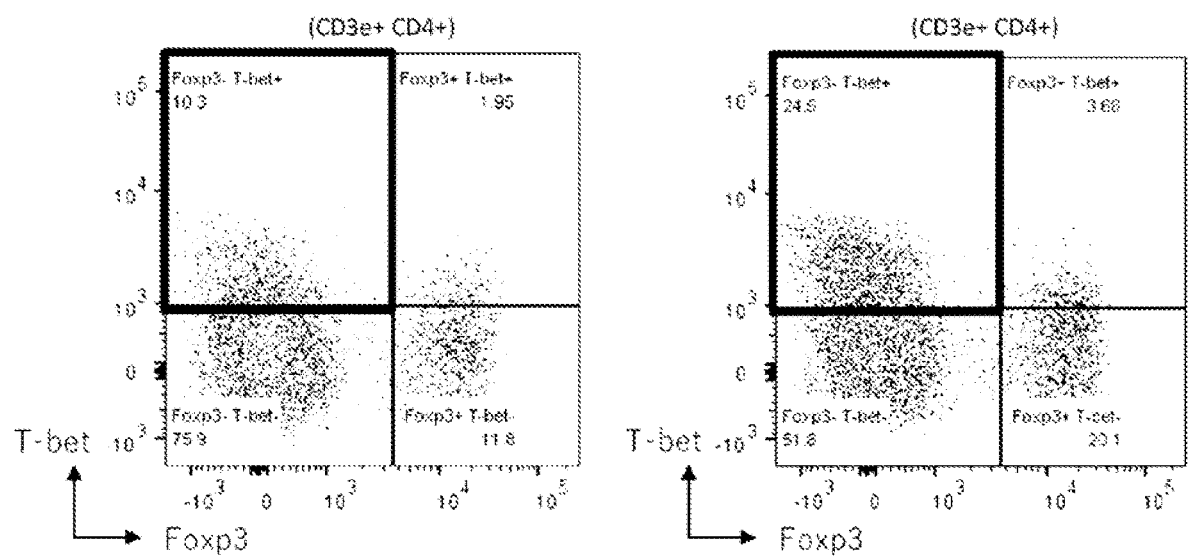
FIG. 4 is diagrams showing flow cytometry results of Th1.

The flow cytometry results are shown in FIG. 4. Of the CD3e-positive and CD4-positive helper T cells, cells not expressing Foxp3 but expressing T-bet were designated as Th1. The ratio of Th1 was higher in the butyric acid diet group with 24.5% than in the normal diet group with 10.3%.

Figure 5:
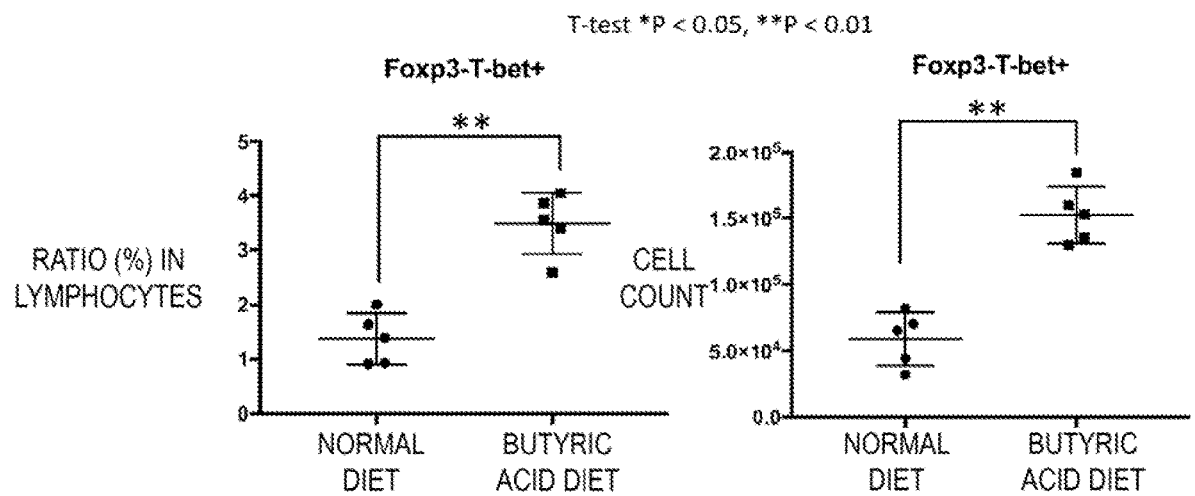
FIG. 5 is diagrams showing quantitative evaluation of Th1 based on flow cytometry.

In addition, the results of quantitative evaluation of Th1 based on flow cytometry are shown in FIG. 5. The ratio of Th1 in the lamina propria lymphocytes was higher in the butyric acid diet group with about 3.5% than in the normal diet group with about 1.5%, where the total number of the lamina propria lymphocytes was regarded as 100, and the number of Th1 was larger in the butyric acid diet group with about $1.5 \times 10^5$ than in the normal diet group with about $5.5 \times 10^4$. The presence or absence of significant difference was evaluated by t-test.

As described above, replacing only 5 wt. % of the purified feed with WSCB sufficiently increased Th1.

Flow Cytometry Results of INF-γ-Producing Cells

Figure 6:
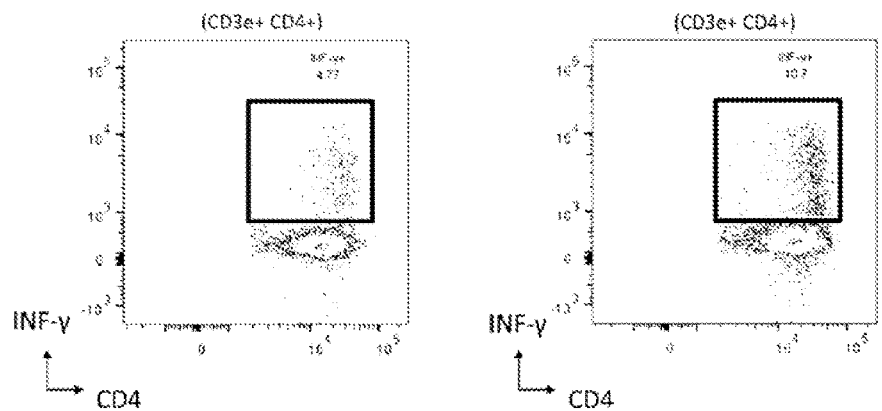
FIG. 6 is diagrams showing flow cytometry results of INF-γ-producing cells.

The flow cytometry results are shown in FIG. 6. Of the CD3e-positive and CD4-positive helper T cells, cells expressing INF-γ were designated as INF-γ-producing cells. The ratio of the cell was higher in the butyric acid diet group with 10.7% than in the normal diet group with 4.8%.

Figure 7:
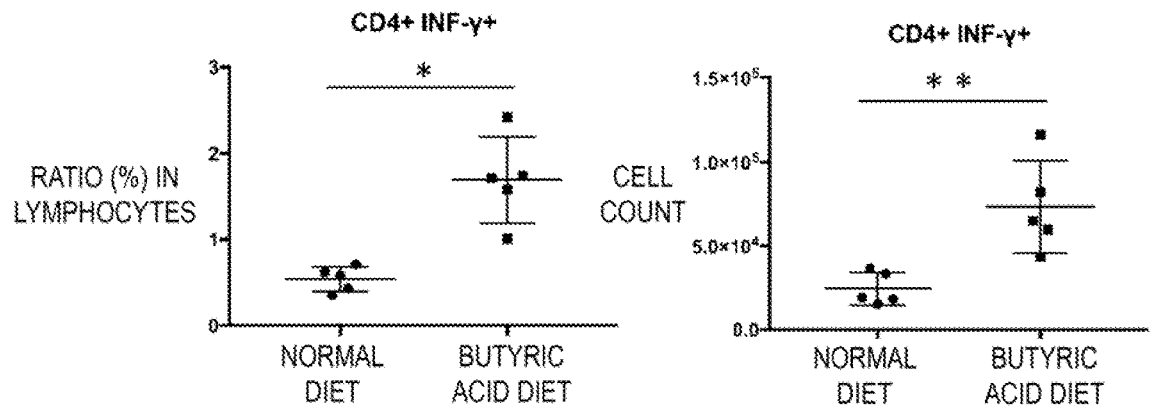
FIG. 7 is diagrams showing quantitative evaluation of INF-gamma producing cells based on flow cytometry.

In addition, the results of quantitative evaluation of INF-γ-producing cells based on flow cytometry are shown in FIG. 7. The ratio of INF-γ-producing cells in the lamina propria lymphocytes was higher in the butyric acid diet group with about 1.6% than in the normal diet group with about 0.5%, where the total number of the lamina propria lymphocytes was regarded as 100, and the number of INF-γ-producing cell was larger in the butyric acid diet group with about $7.5 \times 10^4$ than in the normal diet group with about $2.5 \times 10^4$. The presence or absence of significant difference was evaluated by t-test.

As described above, replacing only 5 wt. % of the purified feed with WSCB increased cells producing INF-γ, the major cytokine of Th1.

Evaluation of Contribution of Enterobacteria in Th1 Increase

Preparation of Feed

Cell-WSCB-AIN-93G (normal diet) and WSCB-AIN-93G (butyric acid diet) were prepared in the same manner as in the evaluation of Th1 increase.

Experimental Animals

C57BL/6J strain male mice aged 3 weeks were used.

Rearing Experiment

Given Cell-WSCB-AIN-93G, 15 individual mice were reared for one week (preliminary rearing). Mice were then grouped into three groups each with five individuals and reared for another four weeks. During this period, one group was given Cell-WSCB-AIN-93G (normal diet) and water. Another group was given Cell-WSCB-AIN-93G (normal diet) and antibacterial agents (drinking water containing a mixture of vancomycin, neomycin, ampicillin, and metronidazole (all from Wako) was administered). Yet another group was given WSCB-AIN-93G (butyric acid diet) and antibacterial agents (drinking water containing a mixture of vancomycin, neomycin, ampicillin, and metronidazole was administered). Administration of four antibacterial agents can effectively reduce enterobacteria and their fluctuations. Thus, whether the increase in Th1 was attributed to WSCB rather than the effect of changes in enterobacteria was verified. Each feed and drinking water were given ad libitum.

Sample Collection

Th1 distal colons were collected from mice of the three groups, the normal diet+water, the normal diet+antibacterial agents, and the butyric acid diet+antibacterial agents, and stored in RNAlater (Thermo Fisher Scientific). Each sample was crushed with stainless beads, and RNA was extracted using RNeasy Mini Kit (Qiagen). In addition, reverse transcription PCR was performed using a random primer and ReverTra Ace (both from Toyobo Life Science).

Quantitative PCR

The expression of the Tbx21 gene encoding T-bet in the distal colon was evaluated by quantitative PCR. Specifically, quantitative PCR was performed using Light Cycler 480 (Roche), and the relative expression of Tbx21 to that of β-actin (Actb), a housekeeping gene, was calculated using the comparative Ct method.

The expression of the Infg gene encoding interferon-γ (IFN-γ) in the distal colon was evaluated by quantitative PCR. Specifically, quantitative PCR was performed using Light Cycler 480 (Roche), and the relative expression of Infg to that of β-actin (Actb), a housekeeping gene, was calculated using the comparative Ct method.

Quantitative PCR Results

Figure 8:
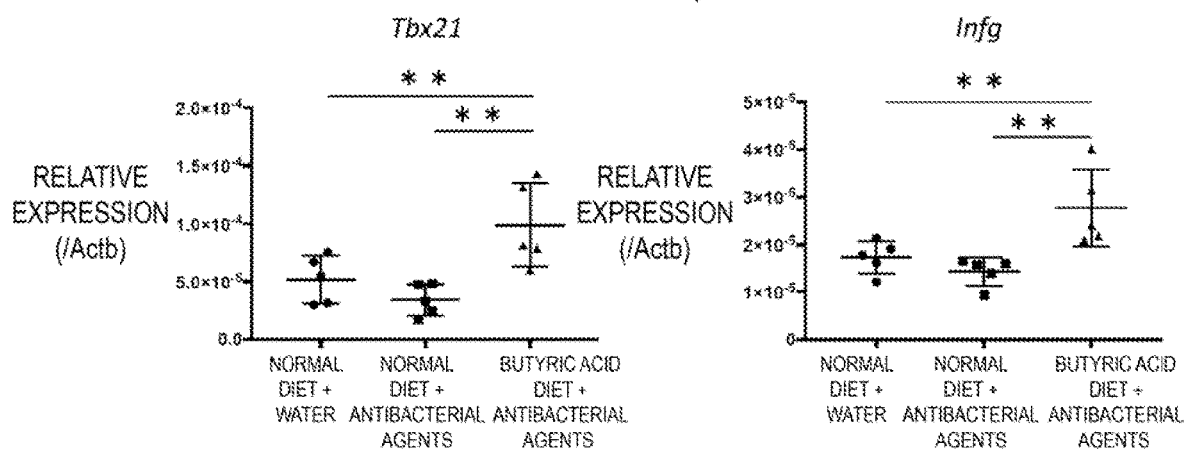
FIG. 8 is diagrams showing quantitative PCR results.

The quantitative PCR results are shown in FIG. 8. The relative expression of the Tbx21 gene in the distal colon was significantly higher in the butyric acid diet group than in the normal diet group also under the administration of antibacterial agents. In addition, the relative expression of the Infg gene encoding INF-γ was significantly higher in the butyric acid diet group than in the normal diet group also under the administration of antibacterial agents. The presence or absence of significant difference was evaluated by one-way analysis of variance (one-way ANOVA) followed by Tukey's test. These results suggest that WSCB induces Th1 regardless of the fluctuations of enterobacteria.

The invention claimed is:

1. A method of increasing type 1 helper T cells, which comprises administering a type 1 helper T cell-increasing agent comprising a cellulose derivative as an active ingredient, the cellulose derivative having a degree of butyryl substitution of 0.3 or greater and 2.6 or less, and a total degree of substitution of 0.5 or greater and 2.8 or less, wherein the increase in type 1 helper T cells treats and/or reduces the likelihood of a tumor.

2. The method according to claim 1, wherein a dose per administration of the type 1 helper T cell-increasing agent is 12.5 mg/kg body weight to 125 mg/kg body weight.

3. A method of increasing INF-γ-producing cells, which comprises administering an INF-γ-producing cell-increasing agent comprising a cellulose derivative as an active ingredient, the cellulose derivative having a degree of butyryl substitution of 0.3 or greater and 2.6 or less, and a total degree of substitution of 0.5 or greater and 2.8 or less.

4. The method according to claim 3, wherein the increase in INF-γ-producing cells treats or reduces the likelihood of a tumor.

5. The method according to claim 4, wherein a dose per administration of the INF-γ-producing cell-increasing agent is 12.5 mg/kg body weight to 125 mg/kg body weight.

6. The method according to claim 3, wherein the cellulose derivative has a degree of butyryl substitution of 0.3 or greater and 1.5 or less, and a total degree of substitution of 0.5 or greater and 1.5 or less.

7. The method according to claim 3, wherein the cellulose derivative has a degree of acetyl substitution of greater than 0 and 2.5 or less.

8. The method according to claim 3, wherein the cellulose derivative has a degree of acetyl substitution of 0.

9. The method according to claim 3, wherein the INF-γ-producing cell-increasing agent is present in a food.

10. The method according to claim 3, wherein the INF-γ-producing cell-increasing agent is present in a food and, which comprises 1 wt. % or greater and 5 wt. % or less of the cellulose derivative.

11. The method according to claim 3, wherein the INF-γ-producing cell-increasing agent is present in a pharmaceutical composition.

* * * * *